United States Patent
Jonasson

Patent Number: 5,082,006
Date of Patent: Jan. 21, 1992

[54] DEVICE FOR PREVENTING INVOLUNTARY MICTURITION

[76] Inventor: Linda Jonasson, Bjornsonsparken 76, DK-9380 Vestbjerg, Denmark

[21] Appl. No.: 469,533
[22] PCT Filed: Sep. 14, 1988
[86] PCT No.: PCT/DK88/00152
  § 371 Date: Mar. 15, 1990
  § 102(e) Date: Mar. 15, 1990
[87] PCT Pub. No.: WO89/02257
  PCT Pub. Date: Mar. 23, 1989

[30] Foreign Application Priority Data
  Sep. 15, 1987 [DK] Denmark ............... 4840/87

[51] Int. Cl.⁵ ..................... A61F 5/48
[52] U.S. Cl. ................ 128/885; 600/29; 600/30; 623/12
[58] Field of Search ........... 128/760–762, 128/768, 769, 885; 604/280, 282, 8, 54, 55; 600/29, 30; 623/12

[56] References Cited

U.S. PATENT DOCUMENTS

| | | | |
|---|---|---|---|
| 3,394,705 | 7/1968 | Abramson | 604/280 X |
| 3,777,755 | 12/1973 | Groves | |
| 3,848,602 | 11/1974 | Gutnick | 604/55 X |
| 4,237,894 | 12/1980 | Cohen | 604/280 X |
| 4,423,725 | 1/1984 | Baran et al. | 604/101 X |
| 4,645,493 | 2/1987 | Ferrando et al. | 604/280 X |
| 4,650,474 | 3/1987 | De Backer | 604/328 X |
| 4,690,677 | 9/1987 | Erb | 604/329 |
| 4,784,651 | 11/1988 | Hickey | 604/280 X |
| 4,909,785 | 3/1990 | Burton et al. | 604/54 |
| 4,930,496 | 6/1990 | Bosley | 604/101 X |
| 4,946,449 | 8/1990 | Davis, Jr. | 604/256 |
| 5,012,822 | 5/1991 | Schwarz | 128/885 |
| 5,036,867 | 8/1991 | Biswas | 128/885 |

FOREIGN PATENT DOCUMENTS

| | | |
|---|---|---|
| 57418/69 | 7/1969 | Australia . |
| 70084/74 | 6/1974 | Australia . |
| 0149391 | 12/1984 | European Pat. Off. . |
| 80090046 | 12/1980 | Sweden . |

*Primary Examiner*—Robert A. Hafer
*Assistant Examiner*—Kerry Owens
*Attorney, Agent, or Firm*—Willian Brinks Olds Hofer Gilson & Lione

[57] ABSTRACT

A device for preventing involuntary micturition, preferably in human females, comprises an oblong, comparatively thin shaft (1). This shaft (1) carries at least one knob (2, 3, 4) forming a thickening on the shaft (1) and being arranged at a distance from the proximal end of the shaft (1). The proximal end of the shaft (1) is provided with a comparatively thin, transverse flap (5).

27 Claims, 1 Drawing Sheet

DEVICE FOR PREVENTING INVOLUNTARY MICTURITION

TECHNICAL FIELD

The present invention relates to a device for preventing involuntary micturition, preferably in human females.

BACKGROUND ART

Numerous devices for preventing involuntary micturition in human females are known. Such devices include for instance a device inserted in the urethra by means of a special instrument, said device expanding in the urethra when the instrument is removed. Such devices are usually difficult to manipulate and irritate a patient during use.

DISCLOSURE OF THE INVENTION

The object of the present invention is to provide a device easy to insert and causing no irritation to a patient carrying the device.

The object of the invention is accomplished by a device comprising an oblong, substantially form-stable, flexible body with varying cross-sectional area depending on the distance from an end of the body and providing at least one knob forming a thickening arranged at a distance from a first end of the body, and that the first end of the oblong body is provided with a comparatively thin, transverse flap, extending substantially perpendicular to the axis of the body.

As a result the inventive device is easily inserted in the urethra and has shown itself to be unproblematic during use. Moreover the device is easily removable, since it can be pressed out by the user during voluntary micturition. Optionally it can also be withdrawn by holding on to the flap. The flap acts also as a safeguard against the device being too deeply inserted in the urethra. Further the inventive device is of special advantage with respect to prevention of involuntary micturition due to its tendency to position itself in such a way that the knobs are located within the strongest sections of the urethral muscles, thus increasing the sphincteral pressure of the urethra.

In an especially preferred embodiment the oblong body is a shaft comprising three mutually spaced knobs.

In accordance with the invention the knob or knobs can be of ellipsoid shape thus achieving an especially gentle and well-functioning co-operation with the surrounding urethral tissue and muscles.

Further in accordance with the invention, the thin, transverse flap can have the form of an annular disc. Thus the inventive device is easy to manipulate during the insertion and the optional withdrawal.

BEST MODE FOR CARRYING OUT THE INVENTION

Figure 1:
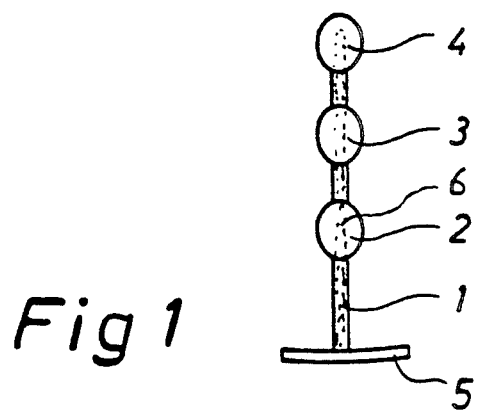
FIG. 1 is a side view of an especially suitable embodiment of an inventive device.

The device of FIG. 1 comprises an oblong body in form of a comparatively thin shaft 1 with three mutually spaced ellipsoid knobs 2, 3 and 4, the knob 4 being at the distal end of the shaft, said end being placed furthest inside the urethra during use. The proximal end of the shaft 1 is provided with a thin disc 5.

In a preferred embodiment the device is of a length of approx. 5 cm, and the shaft 1 is of annular cross-section with a diameter of approx. 2 mm. The knobs 2, 3 and 4 have a mutual distance of approx. 4 mm and their largest diameter measured perpendicular to the shaft is approx. 7 mm. The length of the knobs 2, 3 and 4 is approx. 8 mm, measured in the longitudinal direction of the shaft. The annular disc 5 is of a diameter of approx. 14 mm and of a thickness of less than 0.5 mm. The entire device is suitably integrally made of a comparatively soft plastic material having such a rigidity that it is easily inserted in the urethra. The shaft is optionally hollow to receive an insertion means in form of a long, thin pin. The plastic material is preferably tissue-compatible and desinfecting.

Figure 2:
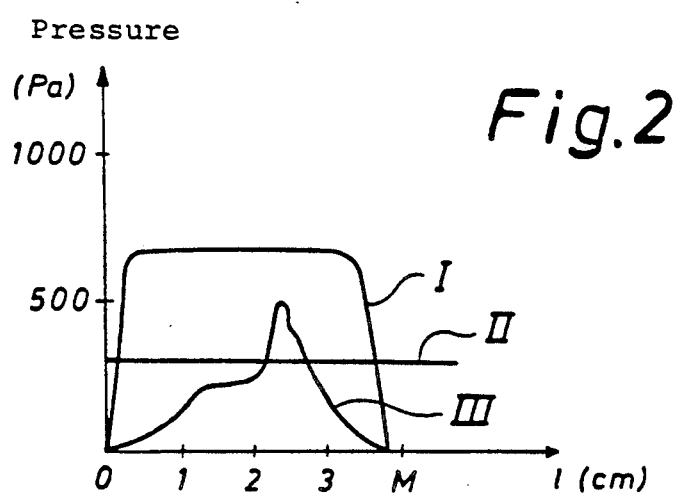
FIG. 2 is a graphic representation of the pressure in the urethra of a person with a normally functioning urethra, and of a patient suffering from urinary incontinence.

The urethra of an adult human female is usually of a length of 3-5 cm and surrounded by muscles over its entire length from the bladder to the external urethral ostium. The strongest muscles of this muscle group are situated adjacent the bladder as well as in the middle of the urethra. These muscles usually seal off the urethra. A graphic representation of the pressure maintaining a sealed urethra in a human female usually follows a curve depicted at I in FIG. 2. The abscissa indicates the length of the urethra measured from the bladder to the external urethral ostium (M), and the ordinate indicates the pressure measured in Pa. Usually the pressure in the urethra is approx. 600-700 Pa. The intravesical pressure of a person standing upright is normally between 300 and 400 Pa, as indicated by means of curve II in FIG. 2. Thus the normal safety margin is approx. 400 Pa over the entire length of the urethra. Curve III of FIG. 2 shows a pressure distribution for the urethra of a patient suffering from incontinence. As is apparent, only a short part of the urethra, i.e. approx. 5 mm, is subjected to a sphincteral pressure higher than the intravesical pressure.

The device of FIG. 1 was tested with the patient on which the pressure distribution of curve III, FIG. 2, was measured. Prior to insertion of the device the ability of the urethra to retain liquids was tested. The bladder was filled with 300 ml water (75% filled), whereupon the person was asked to take the elevator up to the next floor and return via the staircase. This trip was repeated twice. During the experiment the person lost the 300 ml water and additionally approx. 50-100 ml liquid produced during the experiment.

The experiment was then repeated with the device of FIG. 1 inserted in the urethra. During this experiment the person lost only approx. 15 ml.

An examination of the position of the device in the urethra revealed that the knob 2 closest to the disc 5 was about in the middle of the urethra, i.e. within the area where the sphincteral pressure is highest, while the two following knobs were positioned in the vesical ostium and inside the bladder, respectively. It cannot be excluded that the two latter knobs had some effect with respect to retaining liquid, but the presence of three knobs 2, 3 and 4 allows the device to obtain a better position with respect to the muscles of the urinary tract compared to a device with only one knob. By measuring the pressure in the urethra of a patient suffering from incontinence it is apparent where the muscles are strongest, thus permitting the selection of the device best corresponding to the needs of the patient in question. In such a case the distances between the knobs and the annular disc 5 may differ from the ones above.

The above experiment was repeated with other patients, i.a. also with men, and had the same promising results.

A special characteristic of the inventive device is that it turned out to act as a stimulant to the urethral muscles. Experiments have shown that these muscles displayed a temporary increase in strength after use of the inventive device.

The invention is described with respect to a preferred embodiment. Many alterations can, however, be made without thereby deviating from the scope of the invention. The knobs can be of a shape other than ellipsoid. The annular disc can be replaced by a small strip projecting to one side with respect to the shaft. The device can, if so desired, be provided with a cavity (6) as to increase its flexibility. This cavity can for instance open outwardly at the end where the annular disc is located. In such a case the inventive device can be inserted by means of a stiff, oblong means 7 inserted in the cavity (6) and removed after the inventive device has been positioned in the urethra. The number of knobs can, if desired, also differ from the one shown. Instead of a thin shaft with knobs the oblong body can be of larger diameter and provided with a number of recesses.

I claim:

1. A device for preventing involuntary micturition, preferably in human females, comprising a substantially solid oblong, substantially form-stable flexible body with varying cross-sectional area depending on the distance from an end of the body and providing at least one knob forming a thickening arranged at a distance from a first end of the body, said knob sized to pass into the urethra and to retain the device in the urethra, and that the first end of the oblong body is provided with a comparatively thin, transverse flap, extending perpendicular to the axis of the body.

2. A device as claimed in claim 1, characterized in that the oblong body is a shaft (1) having three mutually spaced knobs (2, 3, 4).

3. A device as claimed in claim 1, characterized in that the knob or knobs (2, 3, 4) are of a substantially ellipsoid shape.

4. A device as claimed in claim 1, characterized in that the thin, transverse flap (5) has the shape of an annular disc.

5. A device as claimed in claim 1, characterized in that it is made in form of one integral part of a plastic material.

6. A device as claimed in claim 1, characterized in that the body (1) is provided with a cavity (6) with an opening at the flap (5).

7. A device for preventing involuntary micturition, comprising a thin shaft having a first end, a second end and a closed-ended cavity, said shaft having three mutually spaced, ellipsoidal knobs arranged near the second end, said knobs being sized to pass into the urethra and to retain the device in the urethra, said cavity having an opening at said first end to receive an insertion means, said first end being attached to a thin, transverse flap in the shape of an annular disc, and said device being formed from a single piece of soft plastic.

8. A micturition controlling device comprising:
means for preventing involuntary micturition, said means comprising a closed shaft and having a first end and a second end;

means for positioning the preventing means in the urethra, said positioning means being located on the preventing means near the second end, said positioning means shaped and situated to cooperate with urethral muscles, said positioning means being sized to pass into the urethra and to retain the device in the urethra; and means for facilitating withdrawing the preventing means, said facilitating means being attached to the first end of the preventing means, said facilitating means further preventing the device being too deeply inserted into the urethra.

9. A device as in claim 8, wherein said preventing means comprises a shaft of variable diameter.

10. A device as in claim 9, wherein said shaft comprises at least one knob which is located near the second end of the shaft and which facilitates positioning of the device within the urethra.

11. A device as in claim 10, wherein said knob is of a substantially ellipsoidal shape.

12. A device as in claim 9, wherein said shaft comprises three mutually spaced knobs which are located near the second end of the shaft and which facilitate positioning of the device within the urethra.

13. A device as in claim 8, wherein said facilitating means comprises a transverse flap.

14. A device as in claim 13, wherein said transverse flap has the shape of a thin, annular disk.

15. A device as in claim 8, further comprising means for insertion, said insertion means comprising a cavity in said shaft having an opening at the first end of the shaft and a means for filling the cavity.

16. A device as in claim 15, wherein said filling means is a long, thin pin.

17. A device as in claim 8, wherein said device is made of one integral piece of soft plastic.

18. A device for preventing involuntary micturition comprising:
a substantially solid shaft of variable diameter for preventing micturition, said shaft having a first end and a second end;
at least one knob for positioning the shaft in the urethra, said knob being located on the shaft near its second end, said knob being shaped and situated to cooperate with urethral muscles, and said knob being sized to pass into the urethra and to retain the device in the urethra;
a transverse flap for facilitating withdrawing the shaft, said flap being attached to the first end of the shaft, said flap further preventing the device being too deeply inserted into the urethra.

19. A device as in claim 18, wherein at least one knob comprises three mutually spaced knobs.

20. A device as in claim 18, wherein said knob is of a substantially ellipsoidal shape.

21. A device as in claim 18, wherein said transverse flap has the shape of a thin, annular disk.

22. A device as in claim 18, wherein the shaft, knob, and transverse flap are made of one integral piece of soft plastic.

23. A device as in claim 18, further comprising a pin for insertion, said pin being inserted into a cavity with an opening at the first end of the shaft.

24. A method for controlling involuntary micturition, comprising the following steps:
providing an elongated shaft, said shaft having a first end and a second end, a transverse flap being attached to the first end, and at least one knob being located on the shaft near the second end, said knob being sized to pass into the urethra and to retain the shaft in the urethra;

grasping the shaft by the first end;

inserting the second end of the shaft into the urethra;

leaving the shaft in the urethra until micturition is to be performed; and then removing the device from the urethra to empty the bladder.

25. The method of claim 24, wherein the provided shaft further comprises a longitudinal cavity opening at the first end of the shaft, said method further comprising the following steps:

after grasping the shaft, inserting a long, thin pin into the longitudinal cavity; and after inserting the shaft, withdrawing the long, thin pin from the longitudinal cavity.

26. The method of claim 24, wherein the step of grasping the shaft comprises grasping the transverse flap.

27. The method of claim 24, wherein the step of inserting comprises advancing the shaft into the urethra until only the transverse flap remains outside the urethra.

* * * * *

UNITED STATES PATENT AND TRADEMARK OFFICE
CERTIFICATE OF CORRECTION

PATENT NO. : 5,082,006
DATED     : Jan. 21, 1992
INVENTOR(S) : Linda Jonasson

It is certified that error appears in the above-identified patent and that said Letters Patent is hereby corrected as shown below:

ON THE TITLE PAGE:

Item [75]  Add

--Svend A. Jensen, Barcelona, Spain--

Signed and Sealed this

Twenty-sixth Day of October, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,082,006
DATED : January 21, 1992
INVENTOR(S) : Linda Jonasson

Page 1 of 4

It is certified that error appears in the above-identified patent and that said Letters Patent is hereby corrected as shown below:

On the title page, item [56]:

IN THE REFERENCES CITED

On the title page, column 1, under the heading "U.S. PATENT DOCUMENTS", after "Groves" please insert
--............ 128/271--.

IN THE DRAWINGS

On the drawing page, please delete Fig. 1 and substitute therefor:

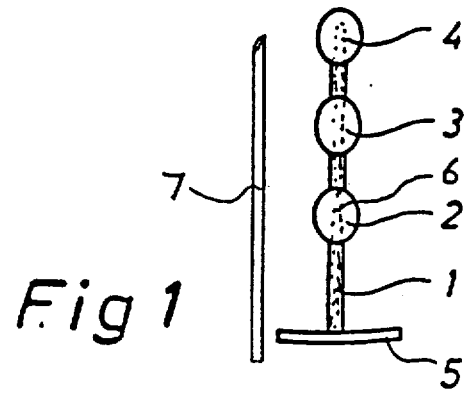

Fig 1

UNITED STATES PATENT AND TRADEMARK OFFICE
CERTIFICATE OF CORRECTION

PATENT NO. : 5,082,006

DATED : January 21, 1992

INVENTOR(S) : Linda Jonasson

It is certified that error appears in the above-identified patent and that said Letters Patent is hereby corrected as shown below:

In column 1, line 32, after "result" please insert --,--.

In column 1, line 34, after "Moreover" please insert --,--.

In column 1, line 36, after "Optionally" please insert --,--.

In column 1, line 39, after "Further" please insert --,--.

In column 1, line 45, after "embodiment" please insert --,--.

In column 1, line 47, after "invention" please insert --,--.

In column 1, line 48, after "shape" please insert --,--.

In column 1, line 49, please delete "co-operation" and substitute therefor --cooperation--.

In column 1, line 51, after "Further" please insert --,--.

In column 1, line 53, after "Thus" please insert --,--.

UNITED STATES PATENT AND TRADEMARK OFFICE
CERTIFICATE OF CORRECTION

PATENT NO. : 5,082,006
DATED : January 21, 1992
INVENTOR(S) : Linda Jonasson

It is certified that error appears in the above-identified patent and that said Letters Patent is hereby corrected as shown below:

In column 1, line 67, before "form" please insert --the--.

In column 2, line 4, after "embodiment" please insert --,--.

In column 2, line 16, before "form" please insert --the--.

In column 2, line 18, please delete "desinfecting" and substitute therefor --disinfecting--.

In column 2, line 23, after "bladder" please insert --,--.

In column 2, line 34, after "Thus" please insert --,--.

In column 2, line 38, after "i.e." please insert --,--.

In column 2, line 43, after "device" please insert --,--.

In column 2, line 45, before "water" please insert --of--.

In column 2, line 48, after "experiment" please insert --,--.

In column 2, line 49, before "water" please insert --of--.

UNITED STATES PATENT AND TRADEMARK OFFICE
CERTIFICATE OF CORRECTION

PATENT NO. : 5,082,006
DATED : January 21, 1992
INVENTOR(S) : Linda Jonasson

It is certified that error appears in the above-identified patent and that said Letters Patent is hereby corrected as shown below:

In column 2, line 57, after "i.e." please insert --,--.

In column 2, line 67, after "incontinence" please insert --,--.

In column 3, line 2, after "case" please insert --,--.

In column 3, line 5, please delete "i.a." and substitute therefor --i.e.,--.

In column 3, line 19, after "can" please insert --,--; after "instance" insert --,--.

In column 3, line 21, after "case" please insert --,--.

In column 3, line 22, please delete "7" and substitute therefore (7).

In column 3, line 26, after "knobs" please insert --,--.

Signed and Sealed this

Seventh Day of June, 1994

BRUCE LEHMAN

Attest:

Attesting Officer

Commissioner of Patents and Trademarks